United States Patent [19]

Oh et al.

[11] Patent Number: 5,307,273

[45] Date of Patent: Apr. 26, 1994

[54] APPARATUS AND METHOD FOR RECOGNIZING CARPETS AND STAIRS OF CLEANING ROBOT

[75] Inventors: Ki Tae Oh; Jin Seong Hwang, both of Seoul, Rep. of Korea

[73] Assignee: Goldstar Co., Ltd., Yongdungpo-Ku, Rep. of Korea

[21] Appl. No.: 750,403

[22] Filed: Aug. 27, 1991

[51] Int. Cl.$^5$ ..................... G06F 13/10; G06G 7/161
[52] U.S. Cl. .................... 364/424.02; 364/424.01; 73/597; 73/646; 901/1; 901/46; 367/99; 367/89; 367/903; 180/167; 180/168; 180/169
[58] Field of Search ............. 364/424.02, 424.01; 367/96, 903, 99, 116, 89, 93, 117, 140, 901; 901/1, 46; 180/167–169; 340/516, 446; 181/123; 73/597, 646

[56] References Cited

U.S. PATENT DOCUMENTS

| | | | |
|---|---|---|---|
| 4,510,587 | 4/1985 | Schneider | 367/96 |
| 4,542,489 | 9/1985 | Naruse | 367/93 |
| 4,674,057 | 6/1987 | Caughman et al. | 901/46 |
| 4,678,056 | 7/1987 | Kobari et al. | 180/167 |
| 4,685,093 | 8/1987 | Gill | 367/89 |
| 4,750,584 | 6/1988 | Tanaka et al. | 181/123 |
| 5,076,384 | 12/1991 | Wada et al. | 364/424.01 |
| 5,086,535 | 2/1992 | Grossmeyer et al. | 180/169 |
| 5,109,566 | 5/1992 | Kobayashi et al. | 901/1 |

FOREIGN PATENT DOCUMENTS 1-207806  11/1989  Japan .
1-232255  12/1989  Japan .

Primary Examiner—Jack B. Harvey
Assistant Examiner—Hal D. Wachsman
Attorney, Agent, or Firm—Brumbaugh, Graves, Donohue & Raymond

[57] ABSTRACT

Apparatus and method for determining the condition of the floor to be cleaned by a cleaning robot. The apparatus comprises an ultrasonic wave signal transmitting circuit for transmitting an ultrasonic wave signal to an ultrasonic wave signal transmitter under the control of a microcomputer, a receiving amplifying unit for amplifying the ultrasonic wave signal transmitted from the ultrasonic wave signal transmitter and received in a ultrasonic wave signal receiver, a receiving demodulating unit for smoothing the output signal from the receiving amplifying unit to demodulate it and then apply it to the microcomputer. According to the control of the microcomputer, the ultrasonic wave signal is transmitted for a predetermined period. The period from the time when the ultrasonic wave signal is transmitted to the time when the ultrasonic wave signal is received in the ultrasonic wave signal receiver is measured. Then, the distance between the position of the ultrasonic wave signal receiver and the floor to be cleaned is calculated from the measured period. Accordingly, it can be determined whether the floor to be cleaned is a normal floor, a floor covered with a carpet, or stairs, thereby enabling correct recognition of the condition of the floor to be cleaned, without being adversely affected from environment.

9 Claims, 7 Drawing Sheets

APPARATUS AND METHOD FOR RECOGNIZING CARPETS AND STAIRS OF CLEANING ROBOT

BACKGROUND OF THE INVENTION

The present invention relates to an apparatus for recognizing floor condition of a cleaner, and more particularly to an apparatus and a method for recognizing carpets and stairs of a cleaning robot, which can determine whether the floor to be cleaned is a normal floor, a floor covered with a carpet, or stairs.

FIGS. 1A and 1B are a side view and a bottom view showing a conventional cleaner with infrared ray transmitter and receiver, respectively. As shown in the drawings, the infrared ray transmitter 4 and the infrared ray receiver 5 are mounted to the front portion of the bottom surface of a cleaner body 1 such that they are vertically spaced about 5 cm apart from the floor to be cleaned. In the drawings, the reference numeral "2" designates wheels and the reference numeral "3" designates a caster.

Referring to FIG. 2, there is shown a circuit for transmitting infrared ray in the conventional cleaner. As shown in the drawing, the circuit which is designated by the reference numeral "6" comprises an oscillating element 7 to which a resistor R21 for supplying a power from a power source Vcc, resistors R22 and R23, a condenser C21 for setting a time constant by cooperating with said resistors R22 and R23, and a transistor Q21 having a base connected with the output terminal P3 via a resistor 24 and a collector connected to a light emitting element, that is the infrared ray transmitter 4 via a resistor R25.

Referring to FIG. 3, there is shown a circuit for receiving infrared ray in the conventional cleaner. As shown in the drawing, the circuit comprises a receiving detector unit 71 which includes resistors R31 to R33, diodes D31 and D32, condensers C31 and C32 and a transistor Q31 and functions to detect the infrared ray received in the infrared ray receiver 5, that is a light receiving element, as a sine wave, a receiving amplifier unit 72 which includes resistors R34 to R40, condensers C33 to C37 and an operational amplifier OP31 and functions to compare the output signal from the infrared ray receiver 5 with an offset voltage and then amplify it, and a receiving demodulator unit 73 which includes inverters IN31 to IN33, a diode D33, a condenser C38 and a resistor R41 and functions to smooth the output signal from said receiving amplifier unit 72 to demodulate it and then apply it to the input terminal PAO of a microcomputer 73.

Operations of the above-mentioned circuits will now be described.

The oscillating element 7 of the infrared ray transmitting circuit 6 generates square wave of 1 KHz according to the time constant set by the resistors R22 and R23 and the condenser C21. The 1 KHz square wave which is outputted from the output terminal P3 of the oscillating element 7 is applied to the base of the transistor Q21 via the resistor R24 so that the transistor Q21 is turned on or off, thereby causing the infrared ray transmitter 4 to transmit infrared ray at the period of 1 msec (=1/1 KHz).

The infrared signals outputted from the infrared ray transmitter 4 as above-mentioned are reflected against the floor and then received in the infrared ray receiver 5. Accordingly, the infrared ray receiver 5 also repeats to be turned on and off at the period of 1 msec so that sine waves are outputted, at the period of 1 msec, from the output terminal of the receiving detector 71 which is connected to the collector of the infrared ray receiver 5.

On the other hand, the amount of the infrared ray signals received in the infrared ray receiver 5 varies depending on the floor condition.

For example, in the case of a normal floor shown in FIG. 4A, all infrared ray signals are directly reflected and received in the infrared ray receiver 5, so that the amount of infrared ray signals received in the infrared ray receiver 5 is greatly different from that in the case that the infrared ray receiver 5 receives no infrared ray. In the case of a carpet covered floor shown in FIG. 4B, however, a part of infrared ray signals transmitted from the infrared ray transmitter 4 are absorbed in the carpet and only the remained part of transmitted infrared ray signals are reflected against the carpet. As a result, the amount of infrared ray signals received in the infrared ray receiver 5 is slightly different from that in the case that the infrared ray receiver 5 receives no infrared ray. On the other hand, in the case of stairs or a very steep surface as shown in FIGS. 4C to 4E, infrared ray signals transmitted from the infrared ray transmitter 4 are reflected from a distant surface and then received in the infrared ray receiver 5. Accordingly, the amount of infrared ray signals received in the infrared ray receiver 5 is slightly different from that in the case that the infrared ray receiver 5 receives no infrared ray.

Depending on such difference in amounts of infrared ray signals received in the infrared ray receiver 5, the amount of current passing through the infrared ray receiver 5 varies. On the other hand, sine wave signals are outputted, at the period of 1 msec, from the output of the receiving detector unit 71 connected to the collector of the infrared ray receiver 5. The amplitude of the sine wave signals is in proportion to the difference between the amount of infrared ray signals received in the infrared ray receiver 5 is slightly and the amount of infrared ray signals in the case that the infrared ray receiver 5 receives no infrared ray. Consequently, the amplitude of sine wave signals outputted from the receiving detector unit 71 is large in the case of FIG. 4A, while it is small in the case of FIGS. 4B to 4E.

These sine wave signals outputted from the receiving detector unit 71 are applied to the inverting input terminal of the operational amplifier OP31, via the condenser C33, the resistor R39 and the condenser C35 of the receiving amplifier unit 72 and then compared with the DC offset voltage predetermined by the variable resistor R35. Thereafter, the compared sine wave signals are amplified at the rate of R38/R39 and then applied to the inverter IN31 of the receiving demodulator unit 73. At this time, if the DC offset voltage is predetermined to the voltage applied to the inverting input terminal of the operational amplifier OP31, when sine wave signals of large amplitude are outputted from the receiver detector unit 71 as in the case of FIG. 4A, low potential signals are outputted from the operational amplifier OP31. Accordingly, the inverter IN31 outputs peak signals of high potential, which is then smoothed at the condenser C38 and the resistor R41, via the diode D33. At this time, the voltages smoothed at the condenser C38 are maintained above a predetermined value, since high potential peak signals are outputted from the inverter IN31, at the period of 1 msec. This smoothed voltages are inverted into low potential signals at the inverter IN32. At the inverter IN33, the low signals are then inverted into high potential signals which is applied to the input terminal PAO of the microcomputer 8. Thus, the microcomputer 8 recognizes that the floor to be cleaned is a normal floor.

On the other hand, when sine wave signals of small amplitude is outputted from the receiving detector unit 71, as in the cases of FIGS. 4B to 4E, the operational amplifier OP31 outputs continuously high potential signals, thereby causing the inverter IN31 to output low potential signals. As a result, low level signals are applied to the input terminal PAO of the microcomputer 8, so that the microcomputer 8 recognizes that the floor to be cleaned is not a normal floor, but a carpet covered floor.

Although the above-mentioned conventional circuit can determine a normal floor and a carpet covered floor, it may mistake stairs or a very steep surface for the carpet covered floor. As a result, there is a disadvantage of providing no protection of cleaning robots from stairs or a very steep surface.

In addition, external light beams may cause malfunction of the circuit in discriminating between a normal floor and a carpet covered floor.

SUMMARY OF THE INVENTION

Therefore, an object of the invention is to provide an apparatus and a method for recognizing carpets and stairs of a cleaning robot, which can determine whether the floor to be cleaned is a normal floor, a floor covered with a carpet, or stairs, without being affected by external light beams.

In one aspect, the present invention provides an apparatus for recognizing carpets and stairs of a cleaning robot, comprising: ultrasonic wave signal transmitting means adapted to frequency-divide an oscillating signal and transmit the frequency-divided oscillating signal under a control of a microcomputer; receiving amplifying means adapted to receive an ultrasonic wave signal transmitted from said ultrasonic wave signal transmitting means and compare-amplify the received ultrasonic wave signal with a DC offset voltage; and receiving demodulating means adapted to demodulate an output signal from said receiving amplifying means smoothly and apply the demodulated signal to the microcomputer.

In another aspect, the present invention provides a method for recognizing carpets and stairs of a cleaning robot comprising the steps of: transmitting an ultrasonic wave signal for a predetermined period (t1) by an ultrasonic wave signal transmitter and according to the control of a microcomputer; measuring the period from the time when the ultrasonic wave signal is transmitted to the time when an ultrasonic wave signal detecting signal is generated as the ultrasonic wave signal is received in an ultrasonic wave signal receiver and then calculating a distance from the measured period; if the calculated distance is no more than the sum of the vertical distance (d1) from the vertical position of said ultrasonic wave signal transmitter and receiver to the floor to be cleaned and a tolerance (e), recognizing the floor to be cleaned as a normal floor; and if the calculated distance is more than the sum of the vertical distance (d1) and the tolerance (e), transmitting the ultrasonic-wave signal again for a predetermined period (t1+a) which is sufficiently longer than said predetermined period (t1), calculating a new distance according to the procedure executed at said calculating step, and if the calculated distance is no more than the sum of the vertical distance (d1) and the tolerance (e), recognizing the floor to be cleaned as a carpet covered floor, while if the calculated distance is more than the sum of the vertical distance (d1) and the tolerance (e), recognizing the floor to be cleaned as stairs.

BRIEF DESCRIPTION OF THE DRAWINGS

Other object and aspects of the invention will become apparent from the following description of embodiments with reference to the accompanying drawings in which:

FIGS. 1A and 1B are views showing an example of conventional cleaner with infrared ray transmitter and receiver, respectively, wherein FIG. 1A is a side view, while FIG. 1B is a bottom view;

FIGS. 4A to 4E are schematic views showing various floor conditions, wherein FIG. 4A shows a normal floor, FIG. 4B a carpet covered floor, FIG. 4C a stairs, FIG. 4D a very steep surface, and FIG. 4E carpet covered stairts;

DETAILED DESCRIPTION OF THE PREFERRED EMBODIMENT

Figure 5:
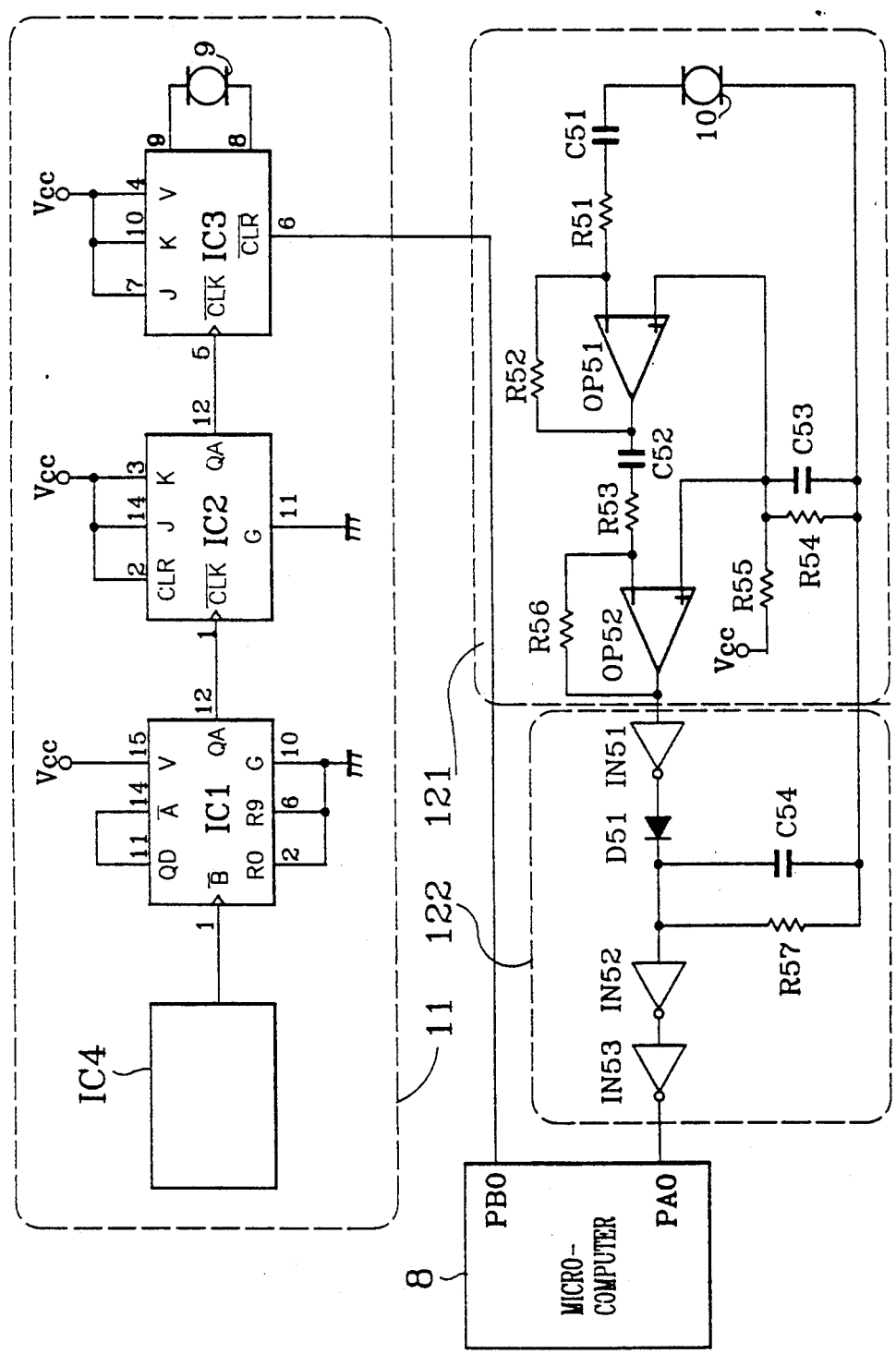
FIG. 5 is a circuit diagram of a circuit for transmitting and receiving an ultrasonic wave signal in a cleaner according to the present invention.

FIG. 5 is a circuit diagram of a circuit for transmitting and receiving an ultrasonic wave signal in a cleaner according to the present invention. As shown in the drawing, the circuit comprises ultrasonic wave signal transmitting means 11 adapted to frequency-divide an oscillating signal and transmit the frequency-divided oscillating signal under a control of a microcomputer 8, receiving amplifying means 121 adapted to receive an ultrasonic wave signal transmitted from the ultrasonic wave signal transmitting means 11 and compare-amplify the received ultrasonic wave signal with a DC offset voltage, and receiving demodulating means 122 adapted to demodulate an output signal from the receiving amplifying means 121 smoothly and apply the demodulated signal to the microcomputer 8. The ultrasonic wave signal transmitting means 11 comprises an oscillating integrated element IC4 for generating the oscillating signal of 1 MHz, a ten frequency-dividing integrated element IC1 for frequency-dividing the oscillating signal from the oscillating integrated element IC4 by ten, a flip-flop IC2 for frequency-dividing an output signal from the ten frequency-dividing integrated element IC1 by two, a flip-flop IC3 for receiving a clear signal from the microcomputer 8 and frequency-dividing an output signal from the flip-flop IC2 by two, and an ultrasonic wave signal transmitter 9 for receiving the two frequency-divided signal from the flip-flop IC3 to transmit the ultrasonic wave signal to the receiving amplifying means 121.

On the other hand, the receiving amplifying means 121 comprises an ultrasonic wave signal receiver 10 for receiving the ultrasonic wave signal from the ultrasonic wave signal transmitter 9 in the ultrasonic wave signal transmitting means 11, an operational amplifier OP51 including its inverting input terminal connected to an output stage of the ultrasonic wave receiver 10 via a condenser C51 and a resistor R51, its non-inverting terminal connected to power source Vcc terminal via a resistor R55 and its output terminal feedback-connected to the inverting input terminal via a resistor R52, and another operational amplifier OP52 including its inverting input terminal connected to the output terminal of the operational amplifier OP51 via a condenser C52 and a resistor R53, its non-inverting terminal connected to the power source Vc terminal via the resistor R55 and its output terminal feedback-connected to the inverting input terminal via a resistor R56. Herein, between the power source Vcc terminal and the non-inverting terminals of the operation amplifiers OP51 and OP52 are connected in parallel to a resistor R54 and a condenser C53.

Also, the receiving demodulating means 122 comprises an inverter IN51 connected to the output terminal of the operational amplifier OP52 in the receiving amplifying means 121, a diode D51 connected to an output terminal of the inverter IN51, an inverter IN52 connected to the diode D51, an inverter IN53 including its input terminal connected to an output terminal of the inverter IN52 and its output terminal connected to an input terminal PAO of the microcomputer 8, and a resistor R57 and a condenser C54 connected in parallel between the diode D51 and the inverter IN52.

Figure 1A:
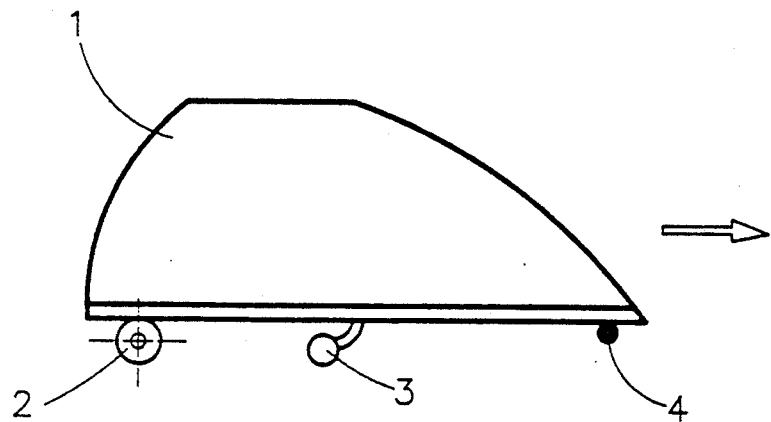
Figure 1B:
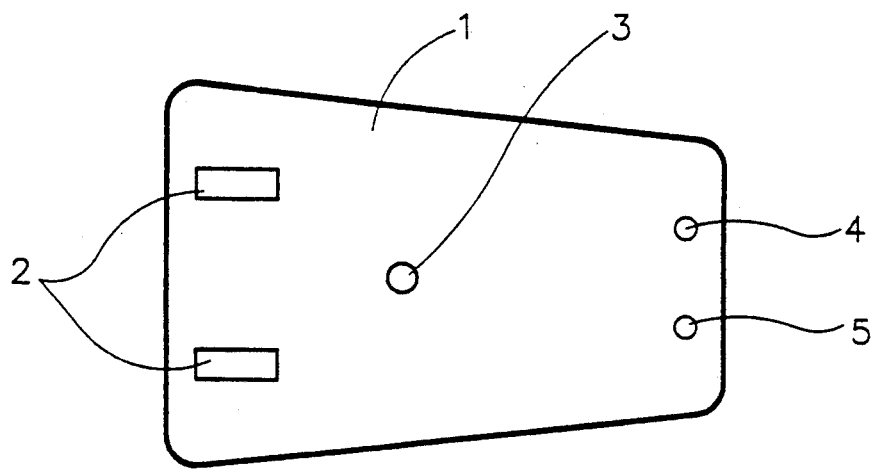
Figure 2:
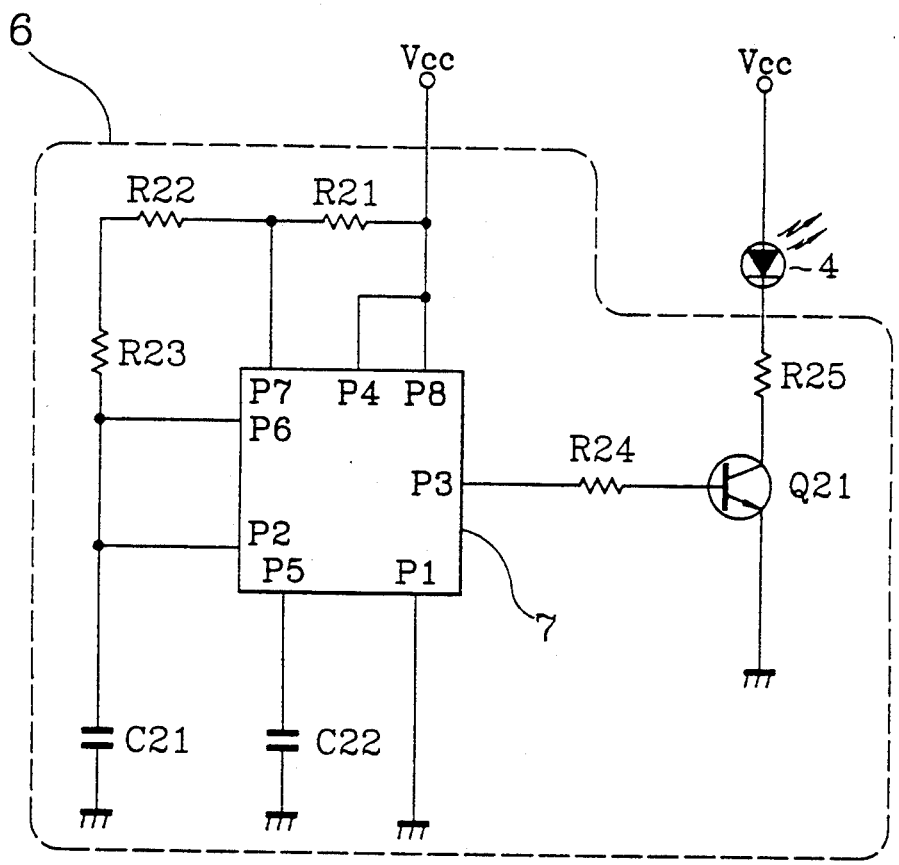
FIG. 2 is a circuit diagram of a circuit for transmitting infrared ray in the conventional cleaner.
Figure 3:
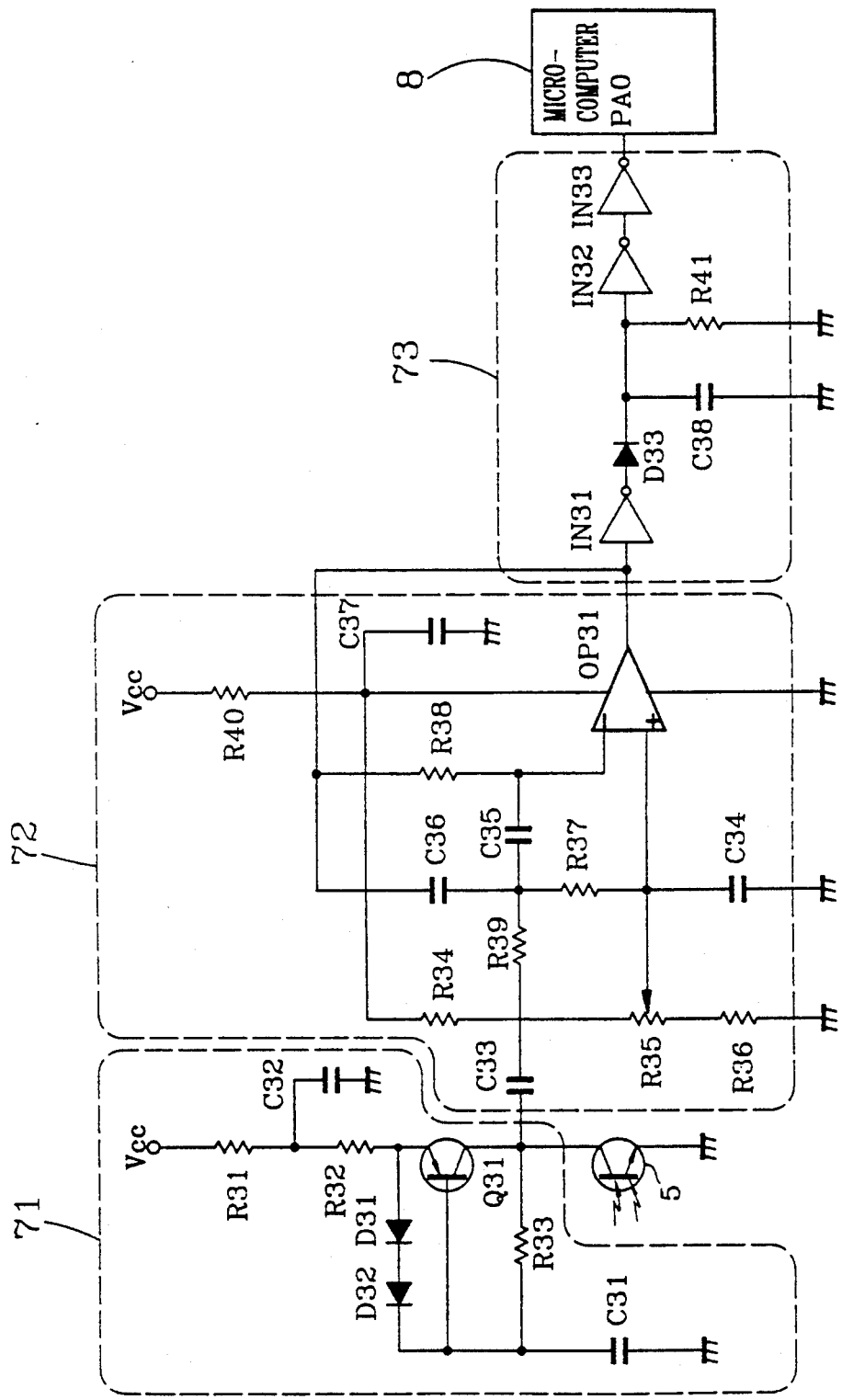
FIG. 3 is a circuit diagram of a circuit for receiving infrared ray in the conventional cleaner.

The ultrasonic wave signal transmitter 9 and the ultrasonic wave signal receiver 10 are used in place of the infrared ray transmitter 4 and the infrared ray receiver 5 shown in FIG. 1. In this case, they are mounted to be vertically apart 10 cm from the floor to be cleaned.

The operation of the circuit with the above-mentioned construction in accordance with the present invention will be described in detail.

First, the oscillation signal of 1 MHz is generated from the oscillating integrated element IC4, which is then frequency-divided by ten by the ten frequency-dividing integrated element IC1. Then, the ten frequency-divided signal is sequentially frequency-divided by two by the two frequency-dividing flip-flops IC2 and IC3. As a result, a square wave signal of 25 MHz is outputted from the flip-flop IC3.

Noticeably, if a low potential signal is outputted from the transmission control terminal PBO of the microcomputer 8, the flip-flop IC3 is cleared so that the ultrasonic wave signal transmitter 9 is not driven; if a high potential signal is outputted from the transmission control terminal PBO of the microcomputer 8, the flip-flop IC3 is released from the clear state and thus outputs the square wave signal of 25 MHz as mentioned above to the ultrasonic wave signal transmitter 9, thereby allowing the transmitter 9 to transmit the ultrasonic wave signal according to the square wave signal of 25 KHz.

Hence, when a high potential signal is outputted from the transmission control terminal PBO of the microcomputer 8 for a predetermined period of transmission time t, the ultrasonic wave signal transmitter 9 transmits the ultrasonic wave signal according to the square wave signal of 25 KHz for the predetermined period of transmission time t, wherein the transmission time t can be controlled softwarely by the microcomputer 8.

Then, the ultrasonic wave signal of 25 KHz transmitted from the ultrasonic wave signal transmitter 9 is reflected from the floor and is then received to the ultrasonic wave signal receiver 10, which then outputs a sinusoidal wave signal of 25 KHz. The amplitude of the sinusoidal wave signal is proportional to the magnitude of the received ultrasonic wave signal. The sinusoidal wave signal outputted from the ultrasonic wave signal receiver 10 is amplified by R52×R56 and the amplified signal is then DC offset by Vcc×R55+R54 by the operational amplifiers OP51 and OP52. Then, the DC offset signal is applied to the input stage of the receiving demodulating means 122.

At this time, the DC offset voltage according to Vcc×R55+R54 is set to a high potential signal which is barely recognized by the inverter IN51 in the receiving demodulating means 122. As a result, a low potential signal is outputted from the operation amplifier OP52 only when the sinusoidal wave signal having the amplitude larger than that of the DC offset voltage is outputted from the ultrasonic wave signal receiver 10, so that a peak signal of high potential is outputted from the inverter IN51. The peak signal of high potential from the inverter IN51 is charged into the condenser C54 through the diode D51 for smoothness. At this time, since the peak signal of high potential is outputted from the inverter IN51 at the period of 25 MHz, the voltage smoothed by the condenser C54 is maintained above a predetermined value. This smoothed voltage is inverted into a low potential signal by the inverter IN52, which is then inverted into a high potential signal by the inverter IN53. In result, this high potential signal is applied to the input terminal PAO of the microcomputer 8.

On the other hand, when the sinusoidal wave signal having the amplitude smaller than that of the DC offset voltage is outputted from the ultrasonic wave signal receiver 10, a high potential signal continues to be outputted from the operational amplifier OP52, thereby causing a low potential signal to be outputted from the inverter IN51. As a result, the charged voltage on the condenser C54 is maintained below a predetermined value, thereby causing a low potential signal to be applied to the input terminal PAO of the microcomputer 8.

In result, when the ultrasonic wave signal receiver 10 receives the ultrasonic wave signal having the magnitude above a predetermined value, a high potential signal is applied to the input terminal PAO of the microcomputer 8 by means of the receiving amplifying means 121 and the receiving demodulating means 122.

Figure 6:
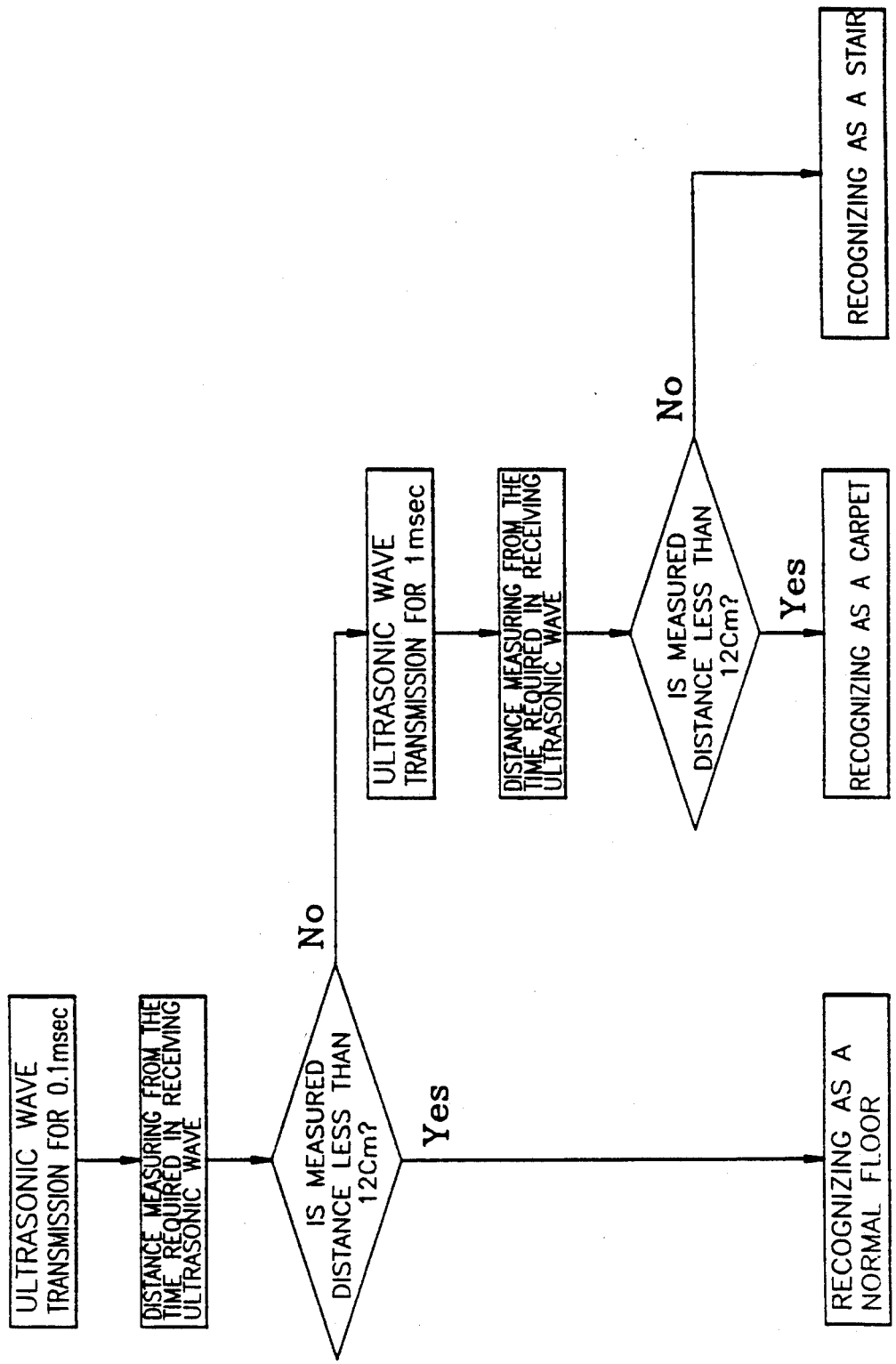
FIG. 6 is a flowchart of a method for recognizing carpets and stairs of a cleaner in accordance with the present invention.

The procedure for determining whether the floor to be cleaned is a normal floor, a carpet covered floor, or stairs will now be described in conjunction with the flowchart of FIG. 6.

During the travel of the cleaning robot, the microcomputer 8 outputs high potential signal at its output terminal PBO, for 0.1 msec, so as to transmit an ultrasonic wave signal for 0.1 msec. Subsequently, the microcomputer 8 checks continuously whether a high potential signal is received in its output terminal PAO, in order to detect the receipt of the ultrasonic wave signal. If the receipt of the ultrasonic wave signal is detected, the period from the time when the ultrasonic wave signal is transmitted to the time when the ultrasonic wave signal is received is measured. At this time, if the receipt of ultrasonic wave signal is not detected until 2 msec lapses after the transmission of ultrasonic wave signal, the ultrasonic wave signal receiving period is regarded as 2 msec. From this measured ultrasonic wave signal receiving period, the distance from the floor can be calculated. That is, the distance is equal to the product of the ultrasonic wave signal receiving period by the acoustic velocity/2.

Figure 4A:
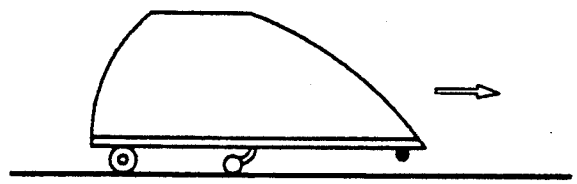

In the case that the cleaning robot travels on a normal floor as shown in FIG. 4A, the ultrasonic wave signal transmitted from the ultrasonic wave signal transmitter 9 is directly reflected against the floor which is vertically apart 10 cm from the bottom of the cleaning robot and then received in the ultrasonic wave signal receiver 10.

Therefore, the calculated distance will be 10 cm ±2 cm, even though a maximum tolerance is taken into consideration.

Figure 4B:
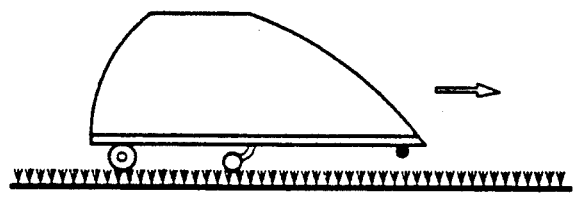

On the other hand, in the case that the cleaning robot travels on a carpet covered floor as shown in FIG. 4B, the ultrasonic wave signal transmitted from the ultrasonic wave signal receiver 10. Accordingly, the ultrasonic wave signal receiving period is regarded as 2 msec, so that the distance is calculated as 34 cm.

Figure 4C:
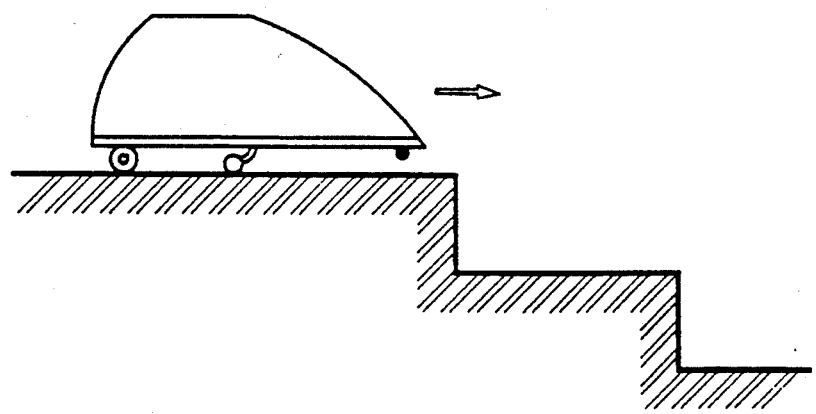
Figure 4D:
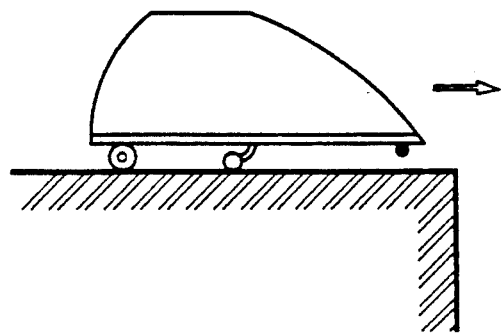
Figure 4E:
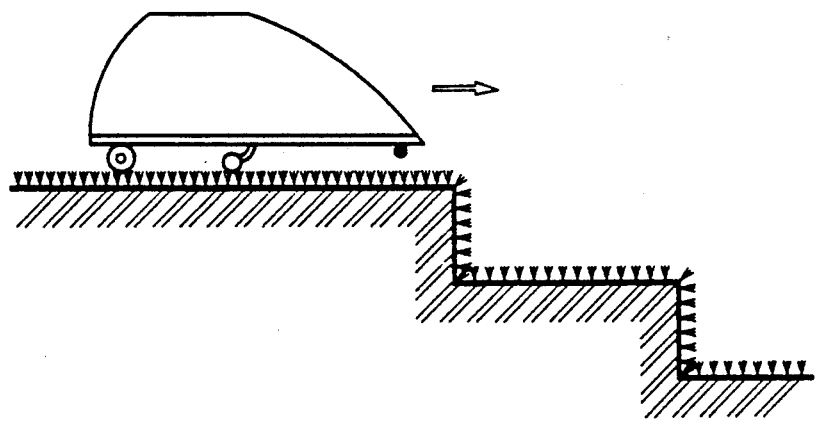

In cases of a very steep surface or carpet covered stairs as shown in FIGS. 4D and 4E, the results are similar to that of the carpet covered floor.

In the case that the cleaning robot travels toward stairs as shown in FIG. 4C, the ultrasonic wave signal transmitted from the ultrasonic wave signal transmitter 9 is hardly received in the ultrasonic wave signal receiver 10 because the stair bottom surface is distantly apart from the bottom of the cleaning robot. When the ultrasonic wave signal is hardly received as above-mentioned, the distance is calculated as 34 cm. When the ultrasonic wave signal is received, the distance from the stair bottom surface is measured as the sum of 10 cm + the stair height ±2 cm.

Accordingly, when the measured distance is no more than 12 cm as the ultrasonic wave signal is transmitted for 0.1 msec, according to the control of the microcomputer 8, the floor to be cleaned is recognized as a normal floor shown in FIG. 4A.

If not the above case, the ultrasonic wave signal is transmitted again for 1 msec. The distance is then measured again in the above-mentioned manner. Even though in the case that the cleaning robot travels on a carpet as shown in FIG. 4B, the ultrasonic wave signal is greatly absorbed in the carpet, it is received in the ultrasonic wave signal. This is because the magnitude of the transmitted ultrasonic wave signal is high, in virtue of the transmission of ultrasonic wave signal for a relatively long period, that is 1 msec. As a result, the distance from the floor to be cleaned is measured as 10 cm±2 cm.

In the case that the cleaning robot travels toward stairs as shown in FIG. 4C, the distance from the stair bottom surface is measured as the sum of 10 cm + the stair height±2 cm. On the other hand, when the cleaning robot travels toward a very steep surface or carpet covered stairs as shown in FIGS. 4D and 4E, the distance is measured as 34 cm, because the ultrasonic wave signal receiver 10 receives no ultrasonic wave signal.

Therefore, when the measured distance is no more than 12 cm as the ultrasonic wave signal is transmitted for 1 msec, according to the control of the microcomputer 8, the floor to be cleaned is recognized as a carpet covered floor shown in FIG. 4B. If not the above case, the floor to be cleaned is determined as stairs or a very steep surface as shown in FIGS. 4C to 4E, so that the microcomputer 8 recognizes that the cleaner robot should travel no longer.

As apparent from the above description, the present invention enables to determine correctly whether the floor to be cleaned is a normal floor, a floor covered with a carpet, or stairs. In accordance with the present invention, there is any possibility of occurring malfunction due to environment.

Although the preferred embodiments of the invention have been disclosed for illustrative purpose, those skilled in the art will appreciated that various modifications, additions and substitutions are possible, without departing from the scope and spirit of the invention as disclosed in the accompanying claims.

What is claimed is:

1. Apparatus for recognizing the condition of a floor comprising:
    (a) first means for transmitting an ultrasonic wave to be reflected off said floor when an actuate signal is provided to said first means; and
    (b) an ultrasonic wave receiver comprising second means for generating an ultrasonic wave receipt signal when said ultrasonic wave reflected on said floor is received by said ultrasonic wave receiver; and
    (c) computing means for providing said actuate signal to said first means for a first time, and testing if said floor is in one of at least three predefined conditions as a function of said first time and the difference in time between when said ultrasonic wave is transmitted and when it is received; and
    (d) if said one of at least three predefined conditions is not the condition of said floor, third means for eliminating this condition as a possibility so it will not be retested, altering said first time, and repeating the steps performed by said computing means and said third means in (c)-(d) until the condition of said floor is determined.

2. Apparatus of claim 1, wherein an initial value of said first time is on the order of 0.1 msec, and is increased to a time on the order of 1 msec if an initial said one of at least three predefined conditions is not the condition of said floor.

3. Apparatus of claim 1, wherein said first means comprises:
    an oscillating integrated element for generating an oscillating signal of predetermined frequency; and
    means for frequency-dividing said oscillating signal under control of said computing means in order to generate said ultrasonic wave.

4. Apparatus of claim 1, wherein three of said at least three predefined conditions comprise a normal condition, a carpeted condition and a step condition.

5. Apparatus of claim 1, wherein said second means comprises:
    means for converting said ultrasonic wave received into an electric signal representing the level of said ultrasonic wave received; and
    means for comparing said electric signal with a reference signal; and
    means for generating or not generating said ultrasonic wave receipt signal as a function of said comparing.

6. The apparatus of claim 5, further comprising means for amplifying said electric signal for better comparison with said reference signal.

7. A method for recognizing the condition of a floor comprising:
    (a) transmitting an ultrasonic wave with an ultrasonic wave transmitter to be reflected off said floor when an actuate signal is provided to said ultrasonic wave transmitter; and (b) generating an ultrasonic wave receipt signal with an ultrasonic wave receiver when said ultrasonic wave reflected on said floor is received by said ultrasonic wave receiver; and (c) providing said actuate signal to said ultrasonic wave transmitter for a first time, and testing if said floor is in one of at least three predefined conditions as a function of said first time and the difference in time between when said ultrasonic wave is transmitted and when it is received; and (d) if said one of at least three predefined conditions is not the condition of said floor, eliminating this condition as a possibility so it will not be retested, altering said first time, and repeating steps (c)–(d) until the condition of said floor is determined.

8. The method of claim 7, wherein an initial value of said first time is on the order of 0.1 msec, and is increased to a time on the order of 1 msec if an initial said one of at least three predefined conditions is not the condition of said floor.

9. The method of claim 7, wherein said generating an ultrasonic wave receipt signal comprises:

converting said ultrasonic wave received into an electric signal representing the level of said ultrasonic wave received; and comparing said electric signal with a reference signal; and generating or not generating said ultrasonic wave receipt signal as a function of said comparing.

* * * * *

UNITED STATES PATENT AND TRADEMARK OFFICE
CERTIFICATE OF CORRECTION

PATENT NO. : 5,307,273
DATED : April 26, 1994
INVENTOR(S) : Ki Tae Oh et al.

It is certified that error appears in the above-identified patent and that said Letters Patent is hereby corrected as shown below:

On the title page, insert : item
--[30]    Foreign Application Priority Data
      August 29, 1990 [KR] Republic of Korea ...13413/1990--.

Signed and Sealed this

Eighteenth Day of October, 1994

Attest:

BRUCE LEHMAN

*Attesting Officer*      *Commissioner of Patents and Trademarks*